United States Patent [19]

Orzalesi

[11] 4,025,552

[45] May 24, 1977

[54] 3-(4'-ALKOXY-BENZOYL)-1,2,2-TRIMETHYLCYCLOPENTANE-CARBOXYLIC ACIDS, METHODS OF USE AND COMPOSITIONS CONTAINING SUCH COMPOUNDS

[75] Inventor: Henri Ange Orzalesi, Montpellier, France

[73] Assignee: Societe Civile de Recherches et d'Etudes Nouvelles (S.C.R.E.E.N.), Paris, France

[22] Filed: Jan. 13, 1975

[21] Appl. No.: 540,504

[30] Foreign Application Priority Data

Jan. 17, 1974 France .............................. 74.01614

[52] U.S. Cl. .............................. 260/520 E; 424/317
[51] Int. Cl.$^2$ .................. C07C 61/36; C07C 65/20; A61K 31/12; A61K 31/19
[58] Field of Search ................. 260/520 E; 424/317

[56] References Cited

UNITED STATES PATENTS

| | | | |
|---|---|---|---|
| 2,132,675 | 10/1938 | Bruson | 260/520 E |
| 3,217,033 | 11/1965 | Kollonitsch | 260/520 E |
| 3,624,210 | 11/1971 | Blye et al. | 260/520 E |
| 3,702,853 | 11/1972 | Edwards et al. | 260/520 E |
| 3,862,239 | 1/1975 | Karmas | 260/520 E |

OTHER PUBLICATIONS

Bleazard et al., "J. Org. Chem.", 1961, pp. 68–73.

*Primary Examiner*—Norman Morgenstern
*Attorney, Agent, or Firm*—Larson, Taylor and Hinds

[57] ABSTRACT

The invention relates to 3-(4'-alkoxy-benzoyl)-1,2,2-trimethyl-cyclopentane-carboxylic acids, and to their optical isomers; they are useful as active principles for anorexigenic drugs.

5 Claims, No Drawings

3-(4'-ALKOXY-BENZOYL)-1,2,2-TRIMETHYLCYCLOPENTANE-CARBOXYLIC ACIDS, METHODS OF USE AND COMPOSITIONS CONTAINING SUCH COMPOUNDS

The invention relates to new compounds, their optical isomers, to a process of preparation thereof and to drugs containing such compounds.

The compounds according to the invention are formed by the 3-(4'-alkoxy-benzoyl)-1,2,2-trimethyl-cyclopentane-carboxylic acids of formula

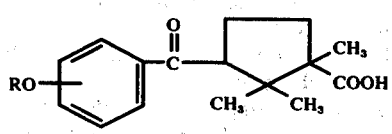

in which OR represents 1 or 2 alkoxy groups fixed on the phenyl group, said alkoxy group being either methoxy or ethoxy groups.

The invention also relates to the optical isomers of these compounds, more particularly to the isomers thereof.

These compounds exhibit important anorexigenic properties, which are all the more unexpected as they contain only carbon, hydrogen and oxygen, whereas, usually, the known anorexigenic compounds also contain nitrogen in their molecule.

The process according to the invention makes use of a condensation of the FRIEDEL & CRAFTS type, in the presence of aluminum chloride as a catalyst.

More particularly, it consists in reacting camphoric anhydrid of formula:

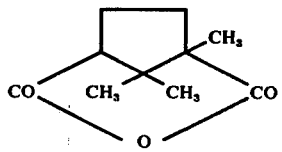

with the corresponding alkoxy-benzene in the presence of aluminum chloride.

Advantageously, the alkoxy-benzene and the camphoric anhydride are added in the form of a mixture to the aluminum chloride, or conversely. If need be said mixture is used in the form of a solution in a common organic solvent such as nitrobenzene or tetrachlorethane.

The isomers of the compounds according to the invention are obtained, in the above process, when starting from the corresponding optical isomers of the camphoric anhydrid.

The invention is hereafter illustrated by examples which have no limitative character.

EXAMPLE 1

The preparation of the levorotatory 3-(4'-methoxy benzoyl)-1,2,2-trimethyl-cyclopentane-carboxylic acid (compound 1):

10 gr. (0.055 mole) of 1-camphoric anhydrid $(\alpha_D^{20°} \quad c = 3.2°)$ are dissolved under stirring in 162 gr. (1.5 mole) of methoxy-benzene.

14.6 gr. (0.11 mole) of aluminum chloride are added portionwise, at ambient temperature and under stirring, to the above solution. After 2 hours of stirring, the reaction mixture is decomposed by ice and a 10% solution of sulphuric acid. The mixture is extracted with ether (in toto 350 ml) and the total ether solution recovered is washed with water. The ether solution is thereafter treated with 100 ml of a 2% aqueous solution of sodium hydroxyde. The alkaline solution obtained is acidified at pH3 with an acid solution, in the present case hydrochloric acid. The crude compound which is isolated is crystallized in benzene. 10 gr. of the above identified isomer are obtained in the form of white crystals. The physical constants of the product according to the invention are as follows:

M P = 176°

$[\alpha]_D^{20°} \quad c = 20°$, 2 (1 = 1; c = 3, chloroform)

main bands in infra-red in cm$^{-1}$ (KBr pellet): 2960, 1690, 1650, 1590, 1235, 1170, 840, 600.

EXAMPLE 2

Preparation of the dextrorotatory 3-(4'-methoxy benzoyl)-1,2,2-trimethyl-cyclopentane-carboxylic acid (compound 2).

The reaction is carried out substantially as in example 1, starting however from the dextrorotatory isomer of camphoric anhydride. 10 gr. of the compound are obtained in the form of white crystals which, after crystallisation in benzene, have a melting point of 165°–166° C.

EXAMPLE 3

Preparation of the racemic compound of 3-(4'-methoxy-benzoyl)-1,2,2-trimethyl-cyclopentane-carboxylic acid (compound 3).

In the same manner, the racemic compound is obtained starting from the racemic form of camphoric anhydride. Its melting point is of 165°–166° C.

EXAMPLE 4

One prepares in the same manner, starting each time from the corresponding alkoxybenzene, the following compounds: 3-(4'-ethoxy-benzoyl)-1,2,2-trimethyl-cyclopentane-carboxylic aicd: MP = 122° C (compound 4)

3 3-(3', 4'-dimethoxy-benzoyl)-1,2,2-trimethyl-cyclopentane-carboxylic acid: MP = 154° C (compound 5).

The compounds according to the invention and their isomers exhibit marked therapeutical properties, particularly anorexigenic properties, as has been shown by pharmacological tests on dogs and rats.

The compound and isomers according to the invention are substantially devoid of toxicity.

Tests were performed on dogs (female Beagle dogs) having an average weight of 10 kg. and which received 100 mg/kg. of compound 1. 30 minutes thereafter they were presented their usual food, but ate less than the third of the average amount of food eaten by controls. The above dose of compound 1 was perfectly tolerated by the animals. It did not induce any substantial change in their general behaviour.

Similar tests were run on male rats of the Wistar type, having an average weight of 150 g. They were divided in groups (each of which comprised 10 animals) which were given orally the compounds 1, 2, 3, 4, and 5 respectively, in the form of a 1% solution of the tested conpounds, at a dose of 1 ml/100 gr. of body weight, during 5 days.

A reduction of the amount of food eaten was observed from the first day. A reduction of the body weight started on the third day.

The L D 50 obtained on mice, for compound 1, were as follows:

orally: 5 gr/kg
intraperitoneally: 500 mg/kg
intraveneously: 125 mg/kg

The compounds and the isomers according to the invention are useful for the treatment of obesity and of excess weight. They are useful for inducing a reduction of the amount of food absorbed by man or animal. They are anorexigen compounds. They can be used as such, or in the form of their physiologically acceptable salts. They are preferably absorbed orally, in admixture either with a solid pharmaceutical carrier or with an orally acceptable solvent.

Therefore, the invention also relates to the solid pharmaceutical compositions containing said compounds and to the drinkable solutions of said compounds.

Daily doses of about 0.200 to about 1 gr., for instance 0.250 gr. can be used. They may be used under dosage units of 0.100 to 0.500 gr.

They can also be administered by the rectal route or by the parenteral route. The invention is also particularly concerned with the compositions containing the compounds according to the invention, in association with suppository carriers, as well as with the injectable solutions containing said compounds in association with an injectable sterile liquid.

I claim:

1. A compound having the formula;

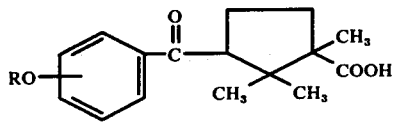

wherein OR represents a member of the group consisting of 3', 4'-dimethoxy, 3', 4'-diethoxy and 4'-ethoxy.

2. 3-(4'-ethoxy-benzoyl)-1,2,2-trimethylcyclopentane-carboxylic acid.

3. 3-(3',4'-dimethoxybenzoyl)-1,2,2-trimethyl-cyclopentane-carboxylic acid.

4. A method for inducing an anorexigenic condition in man or animal which comprises administering to said man or animal an anorexigenic amount of a compound according to claim 1.

5. An anorexigenic composition comprising an anorexigenic amount of a compound having the formula:

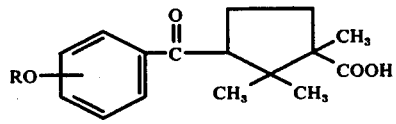

wherein OR represents a member of the group consisting of 3', 4'-dimethoxy, 3', 4'-diethoxy, 4'-methoxy and 4'-ethoxy in association with a pharmaceutically acceptable carrier.

* * * * *